United States Patent
Knott

(10) Patent No.: US 6,572,821 B2
(45) Date of Patent: Jun. 3, 2003

(54) HEART-LUNG MACHINE INCLUDING COMPRESSED FLUID ACTUATED CONTROL MEMBERS

(75) Inventor: Erwin Knott, Poing (DE)

(73) Assignee: Stöckert Instrumente GmbH, Munich (DE)

( * ) Notice: Subject to any disclaimer, the term of this patent is extended or adjusted under 35 U.S.C. 154(b) by 25 days.

(21) Appl. No.: 09/832,629

(22) Filed: Apr. 11, 2001

(65) Prior Publication Data

US 2002/0031442 A1 Mar. 14, 2002

(30) Foreign Application Priority Data

Apr. 11, 2000 (DE) .......................................... 100 17 847

(51) Int. Cl.$^7$ ................................................. A61M 1/14
(52) U.S. Cl. ...................................................... 422/45
(58) Field of Search .............................. 422/45, 46, 47, 422/48, 44; 604/4, 34, 153, 5, 6

(56) References Cited

U.S. PATENT DOCUMENTS

| | | | |
|---|---|---|---|
| 2,590,215 A | 3/1952 | Sausa | |
| 3,552,712 A | 1/1971 | Whitlock | |
| 3,759,289 A | 9/1973 | DeWall | |
| 3,881,483 A | * 5/1975 | Sausse | .................. 210/110 |
| 4,250,872 A | 2/1981 | Tamari | |
| 4,725,037 A | * 2/1988 | Adelberg | ...................... 251/6 |
| 4,925,152 A | 5/1990 | Hüber | |
| 5,814,004 A | 9/1998 | Tamari | |
| 5,927,951 A | 7/1999 | Tamari | |
| 5,957,880 A | * 9/1999 | Igo et al. | ........................ 422/44 |

FOREIGN PATENT DOCUMENTS

| | | |
|---|---|---|
| DE | 25 13 490 | 10/1975 |
| DE | 27 52 087 A1 | 6/1978 |
| DE | 86 10 275.3 | 9/1986 |
| DE | 3811552 A1 | 10/1988 |
| DE | 295 06 422 U1 | 10/1995 |
| EP | 0 659 444 A1 | 6/1995 |
| WO | WO 93/18324 | 9/1993 |
| WO | WO 94/28309 | 12/1994 |
| WO | WO 97/03712 | 2/1997 |

* cited by examiner

Primary Examiner—Henry C. Yuen
Assistant Examiner—Hyder Ali
(74) Attorney, Agent, or Firm—Scully, Scott, Murphy & Presser

(57) ABSTRACT

A heart-lung machine comprises flexible tubing 2, 4, 6, 8 and 10 integrated in an extracorporeal blood circuit of the heart-lung machine. A pump 5 pumps the blood of a patient through at least portions of the extracorporeal circuit. Furthermore, compressed fluid actuated control members 20, 21 are provided acting on one flexible tube 6, 10 of the tubing from without. A control means 11 controls the supply of compressed fluid to the control members. In accordance with the invention the compressed fluid supplied to the compressed fluid actuated control members has an operating pressure in the range 2 to 10 bar.

11 Claims, 2 Drawing Sheets

HEART-LUNG MACHINE INCLUDING COMPRESSED FLUID ACTUATED CONTROL MEMBERS

BACKGROUND OF THE INVENTION

FIELD OF THE INVENTION

The invention relates to heart-lung machines including compressed fluid actuated control members.

In heart-lung machines the blood of a patient is transported in an extracorporeal circuit through flexible tubing and medical apparatus, for example an oxygenator. Transporting the blood in the extracorporeal circuit is done by pumps, more particularly roller pumps, in which the rotor acts from without on a portion of the tubing inserted in the stator of the roller pump. When the rollers applied to the rotor roll along the tubing portion, the tubed blood is delivered by displacement at a velocity of up to 3 m/s.

The extracorporeal circuit needs to be controlled which is usually done by directly influencing the pump or with the aid of compressed fluid actuated or electromechanical control members. When use is made of compressed fluid actuated control members, specially adapted flexible tubing needs to be employed. Thus, known from U.S. Pat. No. 5,814,004 is a system for controlling the pressure in an extracorporeal circuit in which compressed fluid actuated valves are provided to influence the circuit. In this system too, the tubing at the locations at which the compressed fluid actuated control members are provided is designed with a thinner tubing wall so that the compressed fluid of the control member is able to mechanically act on the tubing up to a total closing off of the tubing cross-section.

The disadvantage in this and other known systems for controlling the extracorporeal circuit of a heart-lung machine is that specially configured flexible tubing needs to be employed so as to influence the extracorporeal circuit with the aid of the compressed fluid actuated control members. The tubing needs to be configured at the locations at which compressed fluid actuated control members are required to work, with a changed cross-section and/or a reduced wall thickness or made of some other material which not only makes production more expensive but also hampers handling.

Hitherto, however, this disadvantage has been accommodated or recourse made to electromechanical control members capable of also acting on simple flexible tubing, i.e. tubing not specially prepared for cooperation with the control members. This simple tubing, also termed standard tubing, has substantially a constant cross-section and a constant wall thickness and is made with a consistent material composition, i.e. flexible tubing as usually employed in conjunction with heart-lung machines. Preference is given to this simple tubing by users since it is available in any required length or can be cut to length and because the electromechanical control members can be arranged at any location in the tubing.

Both the electromechanical control members and the compressed fluid actuated control members have hitherto not been put to use for time-critical actions in the extracorporeal circuit of a heart-lung machine, more particularly not for instantly closing off the tubing in an emergency situation, for example, when a bubble detector detects bubbles in the blood transported in the extracorporeal circuit. The reason for this, for one thing, is that electromechanical control members are not deemed reliable enough and, for another, that the compressed fluid actuated control members fail to be quick enough in closing off the tubing.

SUMMARY OF THE INVENTION

It is against this background that the object to be achieved by the invention is to configure a heart-lung machine including compressed fluid actuated control members so that standard flexible tubing can be put to use without portions specially configured for the effect of the control members and which permits fast reliable influencing, more particularly closing off with the aid of the control members so that it is now possible to achieve time-critical actions, such as, for example, closing off the tubing when an air bubble is detected in the extracorporeal circuit.

This object is achieved by a heart-lung machine having the features as set forth in claim 1. Advantageous aspects read from the sub-claims.

In one special aspect the heart-lung machine in accordance with the invention is configured so that when an air bubble is detected in the extracorporeal circuit the supply of the transported blood to the patient is interrupted without the detected air bubble gaining access to the patient.

The gist of the invention is based on the fact that with the aid of a compressed fluid actuated control member a sufficient energy density can be directly made available for influencing standard flexible tubing for controlling the extracorporeal circuit, for example, for closing it off. It is surprising that there is no indication in prior art of using a compressed fluid whose operating pressure is in the range 2 to 10 bar to thus make it possible to close off flexible tubing as normally used with the aid of a compressed fluid actuated control member whilst also achieving time-critical actions. By the invention recoursing to compressed fluid in cited operating pressure usual flexible tubing, so-called standard tubing can now be put to use with no further change in the cross-section, wall thickness or material. The very high operating pressure as compared to that of prior art permits the extracorporeal circuit to be mechanical effected which not only opens up the basic possibility of controlling the extracorporeal circuit but also accommodating the control of time-critical actions. This is due to the fact that by making use of a compressed fluid in the operating pressure range in accordance with the invention of 2 to 10 bar a positively defined closing condition is now achievable due to the high actuating forces.

It is thus particularly of advantage that a compressed fluid having an operating pressure of approximately 5 bar is regularly available in hospitals so that the heart-lung machine in accordance with the invention can be operated there with no additional complication as regards providing the compressed fluid.

It is also of advantage that the compressed fluid actuated control member in accordance with the invention does not come into contact directly with the blood in the extracorporeal circuit since the effect on the non-specially prepared tubing is always from without.

The high pressure level in accordance with the invention of the compressed fluid permits long supply lines which is particularly of advantage in clinical applications when recourse is made to the compressed fluid available at an operating pressure of 5 bar. The heart-lung machine in accordance with the invention may, however, also be retrofitted with a compressor or pressurized bottle which makes the compressed fluid available at the necessary operating pressure for actuating the control members.

In another advantageous aspect the compressed fluid actuated control members are piston spring systems, because it is particularly control members of this kind that are capable of providing very high forces and very high power at the location of the control member, as a result of which a particularly fast reaction is achieved. Control members configured as piston spring systems are thus particularly suitable for use in time-critical systems, for example in conjunction with a bubble detector.

BRIEF DESCRIPTION OF THE DRAWINGS

The invention will now be detailed by way of example embodiments with reference to the attached drawings in which.

DETAILED DESCRIPTION

Figure 1:
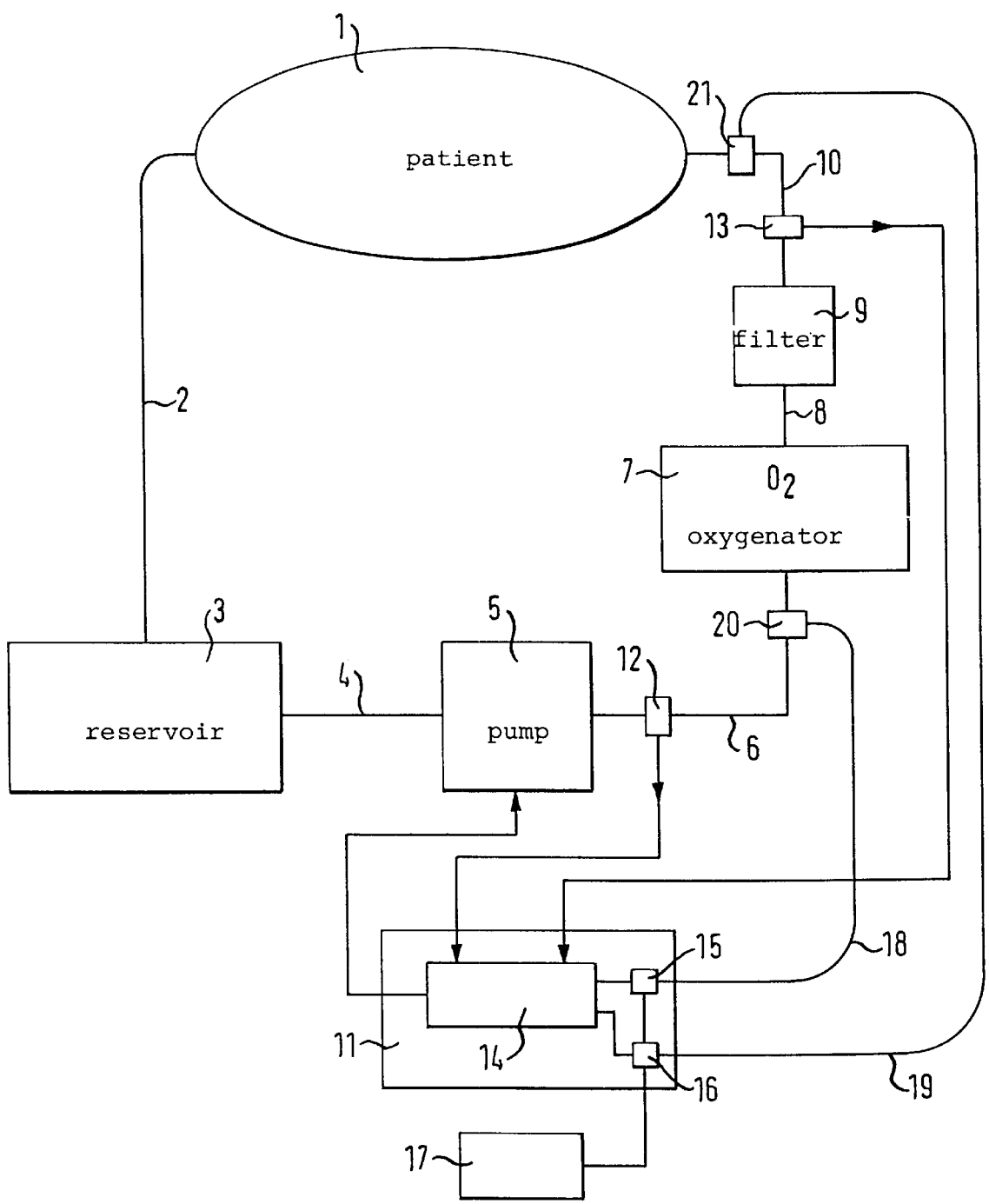
FIG. 1 is a block diagram of a heart-lung machine including control members in accordance with the invention.

Referring now to FIG. 1 there is illustrated, by way of example, the extracorporeal circuit of a heart-lung machine in accordance with the invention, The extracorporeal circuit begins at the patient 1 with a first flexible tube 2 which discharges venous blood of the patient 1 via a cannula. The blood gains access via the flexible tube 2 to a reservoir 3 to which a second flexible tube 4 is connected. Through the second flexible tube 4 the blood gains access from the reservoir 3 to the pump 5 which delivers the blood through the third flexible tube 6 to an oxigenator 7. From here the blood gains access through the fourth flexible tube 8 to a filter 9 before it is returned via the fifth flexible tube 10 and an arterial end cannula connected to the patient 1.

The heart-lung machine in accordance with the invention as shown in FIG. 1 includes in addition a controller 11 to which signals from a first bubble detector 12 and a second bubble detector 13 are supplied. The bubble detectors 12 and 13 are applied to the third flexible tube 6 and fifth flexible tube 10 respectively and monitor the blood transported in the flexible tubing as regards air bubbles occurring therein. As soon as an air bubble occurs in the blood transported by the tubing the bubble detectors 12 and 13 generate a signal which is applied to a processor 14 in the controller 11. The processor 14 opens a first valve 15 or second valve 16 when it receives a signal from the first bubble detector 12 or second bubble detector 13 respectively. The two valves 15 and 16 are connected to a compressed fluid supply means 17 which may be a pressure accumulator, a compressor or the connector of a compressed fluid supply facility of a hospital or the like. The compressed fluid present in the compressed fluid supply means 17 is output via the valves 15 and 16 to a first flexible tube 18 and second flexible tube 19 respectively when the corresponding valve is opened. The compressed fluid tubes 18 and 19 are connected to a compressed fluid actuated control member 20 and 21 respectively. Relative to the first bubble detector 12 the control member 20 is arranged downstream of the third flexible tube 6. Relative to the second bubble detector 13 the compressed fluid actuated control member 21 is arranged downstream of the fifth flexible tube 10.

In accordance with the invention the compressed fluid supply means 17 provides a compressed fluid having an operating pressure in the range 2 to 10 bar, preferably at 5 bar for actuating the compressed fluid control members when the first valve 15 and second valve 16 respectively is opened. Due to the very high operating pressure of the compressed fluid made available in the compressed fluid supply means 17 it is possible in accordance with the invention to provide high mechanical power at the location of the compressed fluid actuated control members 20 and 21 so that fast control actions, more particularly fast switching actions are achievable.

It is thus possible to design the controller 11 so that directly after an air bubble has been detected by one of the bubble detectors 12 or 13 the processor 14 signals the corresponding valve 15 or 16 open to supply the control member 20 or 21 belonging to the bubble detector with the compressed fluid available at high pressure in accordance with the invention via the tubing 18 or 19. The high operating pressure in accordance with the invention results in a fast switching action having a correspondingly low reaction delay so that as soon as an air bubble is detected by one of the bubble detectors the tubing is instantly closed off by the compressed fluid actuated control member located nearest downstream. Preferably the processor 14 then halts the pump, the processor 14 being connected to the pump 5 for this purpose.

The high operating pressure in accordance with the invention also results in the circuit of the control members acting with high reliability.

This reliability can be further enhanced by recoursing to tried and tested control members from other technical fields. This is possible in accordance with the invention since the control members are able to directly effect standard flexible tubing 2, 4, 6, 8 or 10 due to the high operating pressure of the compressed fluid. Standard flexible tubing is, however, regularly very tough so that no damage needs to be feared when using tried and tested high-power control members.

Figure 2A:
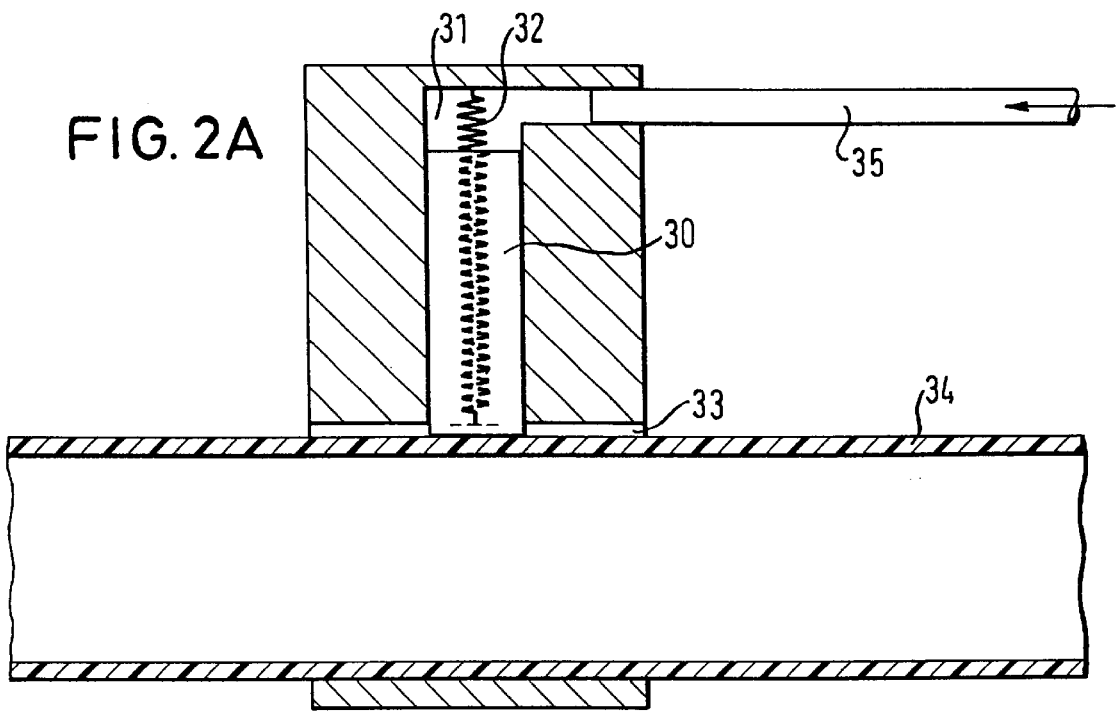
FIGS. 2A and 2B are section diagrams of an example embodiment of a control member in accordance with the invention.
Figure 2B:
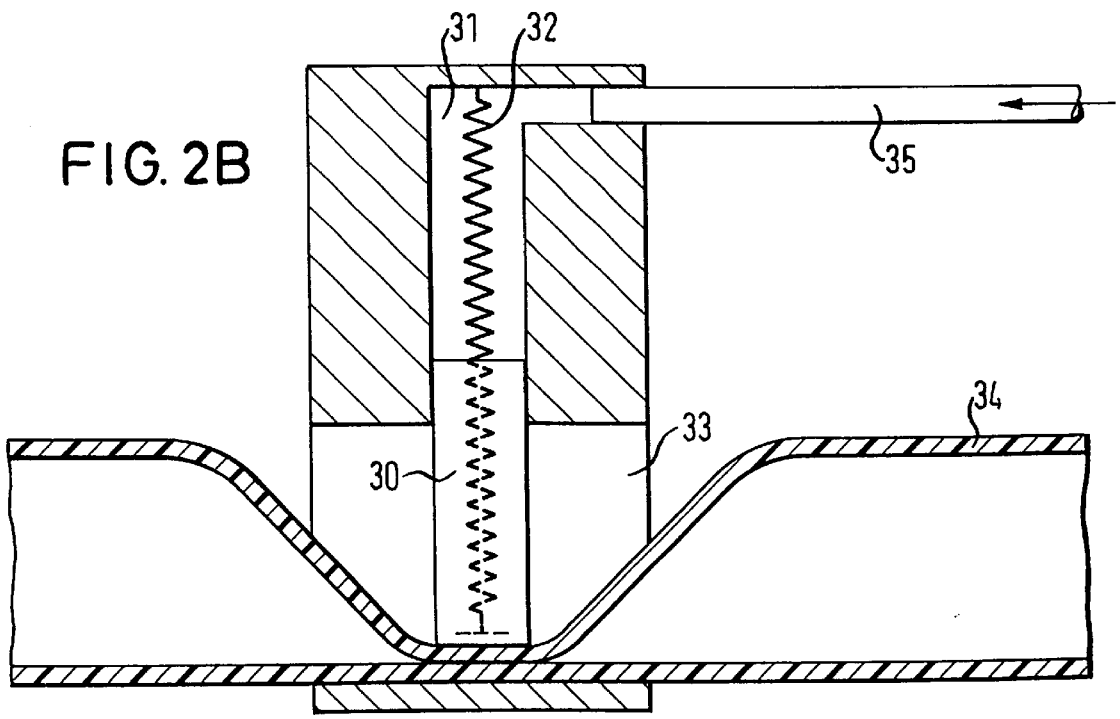

Particularly good results have been achieved with piston spring systems as the compressed fluid actuated control members. Referring now to FIGS. 2A and 2B there is illustrated a piston 30 arranged in a cylinder 31 of one such system in which the cylinder 31 is maintained in the resting position by a spring 32 (FIG. 2A). In this resting position the piston 30 does not effect the tubing 34 inserted in a port 33 of the control member. As soon as the control member receives via the compressed fluid line 35 a compressed fluid which in accordance with the invention is at a high pressure the piston 30 is moved very quickly and with high force against the spring preload and the tubing 34 is closed off as evident from FIG. 2B. It is to be noted in this case that standard tubing or tubing not specially prepared for effecting the control member is made use of as the tubing 34, this being the reason why any flexible tubing usually employed with heart-lung machines can be made use of without requiring any particularly care to providing the compressed fluid actuated control members as long as the high operating pressure of the compressed fluid in accordance with the invention is made available and put to use.

In addition, the high average operating pressure in accordance with the invention ensures that time-critical actions, for example closing off the flexible tubing of the extracorporeal circuit when an air bubble is detected in the blood, are achievable, it being particularly to be noted in this case that the spacing between the bubble detector and the control member closing off the tubing can be selected relatively short since no problems are encountered in the usually occurring flow rates of x m/s of the blood in the tubing and the simultaneous fast response of the control members in accordance with the invention.

The high pressure level in accordance with the invention of the compressed fluid actuating the control members offers the further advantage that very long supply lines are now possible to the compressed fluid actuated control members.

Gases are preferably employed as the compressed fluid. Making use of gases poses no problem especially in the case of piston spring systems or other similar control members since the gas does not directly effect the standard flexible tubing of the extracorporeal circuit, preference being given to e.g. air, helium or nitrogen as gaseous compressed fluids also as regards handling, especially in the operating room environment.

What is claimed is:

1. A heart-lung machine comprising at least one flexible tubing (6, 10; 34) integrated in an extracorporeal blood circuit (2, 3, 4, 5, 6, 7, 8, 9, 10) of said heart-lung machine including at least one pump (5) which pumps the blood of a patient at least through portions of said extracorporeal circuit, at least one compressed fluid actuated control member (20, 21; 30, 31, 32, 33) acting on said flexible tubing (6, 10; 34) from without, and a controller (11) for controlling the supply of compressed fluid to said control member wherein the compressed fluid supplied to the compressed fluid actuated control member has an operating pressure in the range 2 to 10 bar.

2. The heart-lung machine as set forth in claim 1, wherein the compressed fluid supplied to said at least one compressed fluid actuated control member has an operating pressure in the region of approximately 5 bar.

3. The heart-lung machine as set forth in claim 1 wherein said controller (11) is connected to a compressed fluid supply means (17) and comprises at least one valve means (15, 16) to which said compressed fluid is supplied by said compressed fluid supply means (17) and a processor (14) connected to said valve means (15, 16) for its activation.

4. The heart-lung machine as set forth in claim 3 wherein at least one bubble detector (12, 13) for detecting gas bubbles in the blood flow in said flexible tubing as regards the blood low upstream of said at least one compressed fluid actuated control member (20, 21) is provided and wherein said processor (14) for said controller (11) is connected to said bubble detector (12, 13) for receiving a detector signal to switch said valve means (15, 16).

5. The heart-lung machine as set forth in claim 4 wherein said processor (14) on receiving a detector signal from said bubble detector (12, 13) activates said valve means (15, 16) such that said at least one compressed fluid actuated control member (20, 21) closes off said tubing totally before a gas bubble having prompted said detector signal passes said compressed fluid actuated control member in the blood flow.

6. The heart-lung machine as set forth in claim 5 wherein said processor (14) further halts said pump (5).

7. The heart-lung machine as set forth in claim 1 wherein said compressed fluid actuated control member comprises a piston (30) which is moved by a spring (32) into a resting position and which is arranged in a cylinder (31) so that said piston (30) is moved against a spring force when said compressed fluid is supplied to said cylinder (31) and acts on said flexible tubing.

8. The heart-lung machine as set forth in claim 1 wherein said compressed fluid is a gas, more particularly air, helium or nitrogen.

9. The heart-lung machine as set forth in claim 1 wherein said compressed fluid supply means (17) is a compressor.

10. The heart-lung machine as set forth in claim 1 wherein said compressed fluid output means (17) is a compressed fluid bottle.

11. The heart-lung machine as set forth in claim 1 wherein said compressed fluid supply means (17) is an in-house compressed gas supply facility.

* * * * *